United States Patent
Majerski et al.

(10) Patent No.: US 7,094,932 B2
(45) Date of Patent: Aug. 22, 2006

(54) PRODUCTION OF GLYCOLALDEHYDE BY HYDROUS THERMOLYSIS OF SUGARS

(75) Inventors: Piotr A. Majerski, Waterloo (CA); Jan K. Piskorz, Waterloo (CA); Desmond St. A. G. Radlein, Waterloo (CA)

(73) Assignee: Resource Transforms International Ltd., (CA)

( * ) Notice: Subject to any disclaimer, the term of this patent is extended or adjusted under 35 U.S.C. 154(b) by 672 days.

(21) Appl. No.: 10/416,918

(22) PCT Filed: Nov. 8, 2001

(86) PCT No.: PCT/CA01/01562

§ 371 (c)(1),
(2), (4) Date: May 16, 2003

(87) PCT Pub. No.: WO02/40436

PCT Pub. Date: May 23, 2002

(65) Prior Publication Data

US 2004/0022912 A1    Feb. 5, 2004

(30) Foreign Application Priority Data

Nov. 20, 2000   (CA)   .................... 2326471

(51) Int. Cl.
  C07C 45/00    (2006.01)
  A23G 1/00    (2006.01)
(52) U.S. Cl. .................... 568/458; 568/462; 568/465; 568/496; 426/103
(58) Field of Classification Search .................... None
  See application file for complete search history.

(56) References Cited

U.S. PATENT DOCUMENTS

| 4,477,685 A | 10/1984 | Chan |
| 4,503,260 A | 3/1985 | Auvil et al. |
| 4,876,108 A | 10/1989 | Underwood et al. |
| 5,252,188 A | 10/1993 | Stradal et al. |
| 5,292,541 A | 3/1994 | Underwood et al. |
| 5,397,582 A | 3/1995 | Underwood et al. |

OTHER PUBLICATIONS

Toth, et al. "Chemical Aspects of the Smoking of Meat and Meat Products" Advances in Food Research, 1984, p. 137-144, vol. 29, Academic Press Inc., Germany.

Hodge, "Browning Reaction Theories Integrated in Review: Dehydrated Foods" Agricultural and Foods Chemisty, Oct. 1953, pp. 928-943 vol. 1, No. 15.

Kang, et al. "Ketene formation from the Pyrolysis of Carbohydrates" Thermal Uses and Properties of Carboydrates, 1976, pp. 261-273, Academic Press Inc., Richmond, Virginia.

Lowary, et al. "Cycloheptaamylose as a model for starch in the pyrolysis of polysaccharides" Carbohydrate Research 1991, pp. 157-165, vol. 218, Elsevier Science Publishers.

Fagerson "Thermal Degradation of Carbohydrates" Journal of Agriculture Food Chem., Jul.-Aug. 1969, pp. 747-750, vol. 17, No. 4 University of Massachusetts.

Scott, "Productions of Hydrocarbons from Biomass using the Waterloo Fast Pyrolysis Process" DSS-Contract 23283-8-6067, Renewable Energy Div. Jan. 1991, Energy Mines . . . .

Hayashi, et al. "Role-Sugar Fragmentation in an Early Stage Browning of Amino carbonyl Reaction . . . " Agric. Biol. Chem. 1965-70, 1986, vol. 50, No. 8, Nagoya, Japan.

Ruiter, "Colour of Smoked Foods" Food Technology, May 1979, pp. 54-63, Institute of Food Technologies.

Piskorz, et al. "On the Mechanism of the rapid pyrolysis of cellulose" Journal of Analytical and Applied Pyrolysis, 1986 p. 121-137, vol. 9, Elsevier Science Publishers, BV.

Geoghegan, "Reversible Reductive Alkylation of Amino Groups in Protein" Biochemistry, 1979 pp. 5392-5399, vol. 18, American Chemical Society.

*Primary Examiner*—Sikarl A. Witherspoon
(74) *Attorney, Agent, or Firm*—Vermette & Co.

(57)    ABSTRACT

The present invention provides a method for the production of glycolaldehyde with high specificity. The hydrous thermolysis consists of the spraying of aqueous sugar solutions containing from 25 to 80% of water but preferably 30 to 60% water, as a fine mist into a reactor held at the between 500 and 600° C., but preferably between 520 and 560° C. and the condensation of the resulting vaporous product in a surface condenser with optional heat recovery. The residence time of the vaporous product in the reactor should be in the range 0.1–5 seconds, but preferably in the range 0.5 to 2 seconds. Aldose monomeric sugars, preferably glucose (also known as dextrose), are preferred for use in the aqueous solution. The yield of glycolaldehyde in the condensed liquid is minimum 50% by weight of the sugar fed for glucose solutions.

12 Claims, 3 Drawing Sheets

Figure 1: Apparatus for hydrous thermolysis of sugars

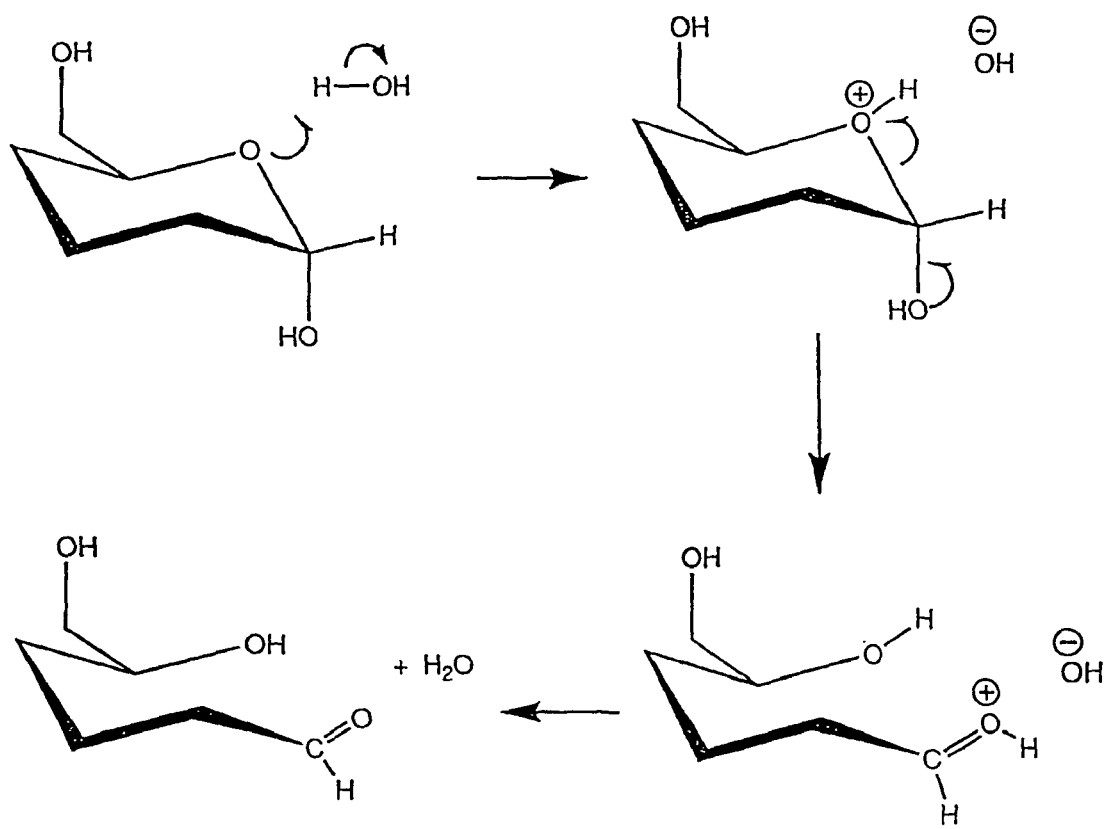
Hypothetical Water-Catalyzed Opening of a Sugar Ring
Fig. 2
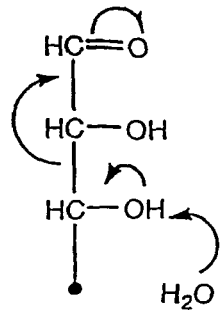
Open-Ring Sugar
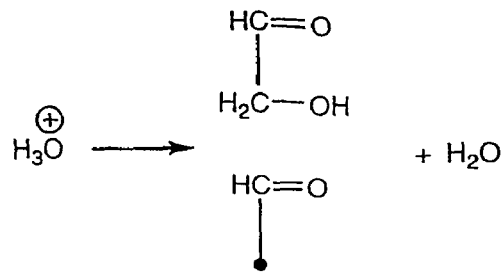
Glycolaldehyde
Hypothetical Water-Catalyzed Retro-Aldol Scission of an Aldose
Fig. 3

PRODUCTION OF GLYCOLALDEHYDE BY HYDROUS THERMOLYSIS OF SUGARS

FIELD

This application is the national stage of PCT/CA01/01562, filed Nov. 8, 2001, and published as WO 02/40436 on May 23, 2002.

This invention relates to solutions of glycolaldehyde and more particularly to an improved process, involving hydrous thermolysis, for preparing them.

BACKGROUND

Glycolaldehyde (also known as hydroxyacetaldehyde) is a well-known and desirable compound that is a useful intermediate for the preparation of other valuable products. There are applications for the pure compound, its aqueous solutions, and solutions containing mixtures of glycolaldehyde and other low molecular weight carbonyl compounds.

For example, glycolaldehyde may be applied as a cross-linking agent for proteinaceous materials (K. F. Geoghegan et al., "Reversible reductive alkylation of amino groups in proteins", Biochem. Vol. 18, 5392–5399, 1979) and other amino containing materials. One advantageous application of glycolaldehyde in this manner is its use in the strengthening of sausage casings.

One particular class of application where glycolaldehyde or its mixtures with other small aldehydes are especially useful is as browning promoters for food colouring and flavouring applications. Various types of browning reactions are known to occur in the cooking of foods. The most important type is the amino-carbonyl reaction (also known as the Maillard Reaction) in which aldehydes, ketones and reducing sugars react with amines, amino acids and proteins.

It has long been known that glycolaldehyde and certain other small carbonyl compounds have very desirable properties as browning agents for foods. For example, in a review in 1953 ("Browning Reaction Theories Integrated in Review. Dehydrated Foods. Chemistry, Vol. 1, Oct. 14, 1953), J. E. Hodge pointed out that glycolaldehyde, glyceraldehyde, pyruvaldehyde, dihydroxyacetone, acetoin and diacetyl, which form upon thermal disintegration of sugars, are some of the most highly reactive browning compounds. Furthermore, Hodge indicated that glycolaldehyde is a product of the thermal fragmentation of sugars on heating their aqueous solutions.

In his review (A. Ruiter, "Color of Smoked Foods", Food Technology, May, 1979, pp54–63) Ruiter discussed the importance of glycolaldehyde and other carbonyl compounds found in liquid smokes, as active browners.

Later on, Hayashi and Namiki, ("Role of Sugar Fragmentation in an Early Stage Browning of Amino-carbonyl Reaction of Sugar with Amino Acid", Agric. Biol. Chem., Vol. 50, pp 1965–1986, 1986) made a quantitative study of the relative efficacies of various carbonyl compounds in the amino-carbonyl reaction. They defined the "browning ability" of the carbonyl compound as being inversely proportional to the time taken for the Optical Density (OD) of the reaction product mixture of the amino acid alanine and the carbonyl compound to reach a specified value. They found that among the $C_2$ and $C_3$ carbonyl compounds produced by fragmentation of sugars, glycolaldehyde had the highest browning ability. Thus the data of Hayashi and Namiki make it quite clear that glycolaldehyde has superior browning properties in the Maillard reaction.

In their U.S. Pat. No. 4,876,108, Underwood at al introduce a "browning index" as being proportional to the OD of the reaction product mixture of the amino acid glycine and the carbonyl compound(s), after a specified period of time. It is therefore expected that this index will be directly proportional to the "browning ability" defined by Hayashi and Namiki so that both indices will give a similar ordering of the browning power of aldehydic solutions resulting from the pyrolysis of carbohydrates.

In their comprehensive review (L. Toth and K. Potthast, "Chemical Aspects of the Smoking of Meat and Meat Products", Advances in Food Research, Vol. 29, pp87–158, 1984, Toth and Potthast summarize earlier and extensive works which show clear correlations between a smoky flavour and the phenolic content of typical "liquid smoke" products. Fujimaki et al ("Analysis and comparison of flavor constituents in aqueous smoke condensates from various woods", Agricultural and Biological Chem., Vol. 38, p45, 1974) concluded that apart from phenols, smoke flavor is due mainly to carbonyls and lactones with higher boiling points.

In summary, the prior art establishes that low molecular weight carbonyl compounds, especially glycolaldehyde, produced by the decomposition of sugars and other carbohydrates are excellent browning agents while the smoky flavor of typical liquid smoke products is due principally to phenols.

Not all fission products of sugar are effective browning agents. For example, formaldehyde is not only inactive, but has been said to be an inhibitor of the amino-carbonyl and other types of browning reactions (Ruiter, 1979).

As formaldehyde is well known to be a hazardous substance, it would be desirable to minimize the amount of formaldehyde by-product and to maximize the ratio of glycolaldehyde to formaldehyde in a glycolaldehyde mixture or aqueous solution. Minimizing formaldehyde production is of particular importance where the glycolaldehyde solution is intended as a food browning agent.

With regard to the production of glycolaldehyde, its preparation from dihydroxymaleic acid is well known. However, this method is ill suited to large-scale production of glycolaldehyde and is impractical for industrial usage. Accordingly, several alternative methods and processes for production of glycolaldehyde are found in the prior art.

Chan (U.S. Pat. No. 4,477,685) and Auvil (U.S. Pat. No. 4,503,260) have disclosed processes for catalytic synthesis of glycolaldehyde from mixtures of carbon monoxide and hydrogen. However, these processes require high pressure and expensive catalysts. There have been several methods disclosed for the vapour phase catalytic conversion of ethylene glycol to glycolaldehyde, e.g. Seto et al, Japan Official Patent Gazette, Dec. 10, 1991, 91279342. However, such methods suffer drawbacks such as low conversion, low yields of glycolaldehyde, and formation of high concentrations of byproducts.

An alternative approach to glycolaldehyde production is through the use of thermochemical methods. It has long been known that glycolaldehyde is a product of the pyrolysis of ligno-cellulosic materials; however, yields were typically very small. Scott et al. discovered that relatively large yields of glycolaldehyde could be obtained from cellulosic feedstocks under so-called fast pyrolysis conditions (J. Piskorz, D. Radlein and D. S. Scott, "On the mechanism of the rapid pyrolysis of cellulose", J. Anal. Appl. Pyrol., Vol. 9, 121–137, 1986). The observations of Scott et al. subsequently led to the patenting of a fast pyrolysis process for producing liquid smoke rich in glycolaldehyde (Underwood and Graham, U.S. Pat. Nos. 4,876,108 and 4,994,297).

Scott has also described the production of glycolaldehyde by the pyrolysis of starch ("Production of Hydrocarbons from Biomass using the Waterloo Fast Pyrolysis Process", DSS Contract 23283-8-6067, Renewable Energy Div., Energy Mines and Resources Canada, Ottawa, Canada, January 1991). The maximum yiled of glycolaldehyde was only 15%.

Pyrolysis of monosaccharides and oligosaccharides including sugars is also well known to produce glycolaldehyde among other carbonyl compounds. For example, Fagerson ("Thermal Degradation of Carbohydrates, A Review", J. Agric. Food Chem., Vol. 17, 747–750, 1969) reported the presence of glycolaldehyde in the pyrolysates of glucose and other carbohydrates in dry systems. It is pointed out that the major volatile products from the pyrolysis of starch, cellulose, sucrose, maltose and glucose were essentially identical.

Kang et al ("Ketene formation from carbohydrates", in "Thermal uses and properties of carbohydrates", F. Shafizadeh, K. V. Sarkanen and D. A. Tillman (eds.), Academic Press, N.Y., 1976) obtained up to 16% of ketene from pyrolysis of glucose, among other sugars, at an optimal temperature of 700° C. Since they also found that ketene could form semi-quantitatively from glycolaldehyde, they concluded that ketene probably formed by a mechanism involving the first formation of glycolaldehyde from glucose. The yield of ketene from fructose was only 8% under the same conditions and that from sorbitol only 0.9%. The implication of this work by Kang et al is that some sugars are likely to give enhanced yields of glycolaldehyde. Lowary and Richards, (Carbohyd. Res., Vol. 218, pp157–166, 1991) have also reported a yield of 12.8% by weight of glycolaldehyde by the vacuum pyrolysis of the cyclodextrin cycloheptaamylose, as a starch model compound, catalysed by trace amounts of sodium chloride.

With respect to the hydrous thermolysis of sugars, their fragmentation in aqueous solutions was first reported by Nodzu (R. Nodzu, Bull Chem. Soc. Japan, Vol. 10, 122–130, 1935). However, although there were indications of small amounts of glycolaldehyde, the principal carbonyl compounds identified were acetol, pyruvaldehyde, diacetyl and pyruvic acid. Sattler and Zerban ("Volatile Decomposition Products of Sugars in Aqueous Solutions", J. Am. Chem. Soc. Vol. 70, 1975, 1948) also pointed out that distillation of sugars from 5% sodium bicarbonate solutions gave a "relatively large" amount of acetol among the volatile products but little glycolaldehyde.

It was noted by Scott ("Chemicals and Fuels from Biomass Flash Pyrolysis", DSS Contract 38ST 23216-6-6164, Renewable Energy Branch, Energy Mines and Resources Canada, Ottawa, Canada, February 1988) that addition of water to the pyrolysis liquid caused separation of a heavy tar phase with enrichment of glycolaldehyde in the supernatant aqueous phase. Scott also taught the removal of colour and phenolic materials from the aqueous phase by extraction with water-insoluble solvents like methylene chloride and by absorption on ion exchange resins.

Stradal et al. subsequently patented processes for the production of "precipitated glycolaldehyde" by pyrolysis of carbohydrate containing feedstocks (U.S. Pat. No. 5,252,188, "Process for producing hydroxyacetaldehyde", issued Oct. 12, 1993) and the use of said "precipitated glycolaldehyde" for food browning applications (U.S. Pat. No. 5,393,542, "Process for producing hydroxyacetaldehyden", issued Feb. 28, 1995). The precipitated glycolaldehyde was produced from the pyrolysis liquid product by water-separation of the pyrolysis liquid and subjecting the obtained aqueous extract to a combination of multiple distillation steps followed by a solvent-induced precipitation.

In U.S. Pat. No. 5,292,541, issued Mar. 8, 1994 and U.S. Pat. No. 5,397,582, issued Mar. 14, 1995, Underwood et al. disclose a method for producing a browning liquid product by pyrolyzing sugars and starches. The pyrolysis process involves heating the sugars or starches at rates of greater than 1000° C. per second under conditions in which the vapour residence time is preferably less than 0.6 seconds and quenching of the volatile product to less than 300° C. in less than 0.6 seconds.

Following the method of Underwood et al., sugars or starches are pyrolyzed, the unpyrolyzed material and solid byproducts are separated from the vaporous products of pyrolysis which are then condensed or, alternatively, quenched with water or the cooled re-circulated product itself to produce a water soluble product. The water-soluble product is then purified by concentration and extraction with a water-insoluble organic solvent. Optionally, the water-soluble product may be further contacted with an ion-exchange resin and finally diluted with water to produce the desired product.

The multiple extraction and purification steps required demonstrate that this method produces a significant amount of undesired by-products along with the glycolaldehyde, which must be removed at additional expense by the stated methods. The final products are solutions relatively rich in glycolaldehyde marketed under the trade name Maillose™.

Unsurprisingly in view of the prior art, the product is claimed to have good browning properties but weak smoke flavor.

Although Underwood et al. have mentioned the use of solutions of sugars as feedstocks in U.S. Pat. No. 5,397,582, issued Mar. 14, 1995, it is clear from their examples that they have not found or recognized the great benefits that can be realized by pyrolyzing dilute solutions of aldose sugars according to the method disclosed herein. They describe the pyrolysis of dextrose (glucose) powder to give a glycolaldehyde yield of only 21.3% by weight of the glucose.

Underwood et al. also present the results of tests designed to elicit the tendency of various sugars to yield glycolaldehyde on pyrolysis. These tests involved the pyrolysis at 250° C. within a gas chromatograph of 5% aqueous solutions of sugars. The results suggest that glucose and sucrose in particular are among the worst possible candidates, giving only 900 and <10 ppm respectively of glycolaldehyde.

In the '541 patent, Underwood et al. assert that the "theoretical yield" of glycolaldehyde from pyrolysis of sugars is 38%. Surprisingly, we have now found that pyrolysis of aqueous solutions of some sugars, especially glucose, under certain conditions result in glycolaldehyde yields up to 70% by weight of the sugar. The surprising yields from the present inventive method are nearly double this supposed limit and therefore suggest the assumptions on which their "theoretical yield" are based are incorrect.

Overall, there is an ongoing need for an improved method of producing glycolaldehyde-rich solutions from inexpensive feedstocks, with as large a yield as possible and with minimum amounts of other compounds, especially formaldehyde. There are also advantages to a method that allows production of glycolaldehyde-rich solutions that can be used for food-browning and other applications with only minimal treatment.

SUMMARY OF THE INVENTION

The present invention provides a method for the production of glycolaldehyde with high selectivity and specificity. The method uses a process of hydrous thermolysis consisting of atomizing an aqueous sugar solution containing from 25 to 99% water but preferably from 30 to 70% water, as a fine mist into a reactor. The reactor is held at a temperature of between 500 and 600° C., but preferably between 540 and 580° C. The resulting vapourous product is condensed in a surface condenser with optional heat recovery and finally filtered to give the product solution. The residence time of the vaporous product in the reactor is in the range of 0.1 to 5 seconds, but preferably in the range of 0.5 to 2 seconds. Aldose monomeric sugars, preferably glucose (also known as dextrose), are preferred for use in the aqueous solution. The yield of glycolaldehyde in the condensed liquid is a minimum of 30% by weight of the sugar contained in the aqueous solution.

The pyrolysis of dilute aqueous sugar solutions containing 30% or more by weight of water (as called hydrous thermolysis) greatly enhances the yield of glycolaldehyde and at the same time, minimizes the formation of formaldehyde and other undesirable by-products. The resulting light golden coloured solution can be used as is for imparting colour to food preparations without having to undergo expensive clean-up procedures like solvent-extraction or absorption on resins. Furthermore, the resulting solution can be obtained without the additional expense of rapid water quenching of the vaporous products of thermolysis. Instead, simple surface condensers suffice to condense the products, which has the further benefit that heat recovery systems can be employed, which is impossible with existing water quench systems.

BRIEF DESCRIPTION OF THE DRAWINGS

Further features and advantages will be apparent from the following detailed description, given by way of example, of a preferred embodiment taken in conjunction with the accompanying drawings, wherein:

FIG. 2 is a theoretical mechanism by which water may catalyze the ring opening of the sugar; and FIG. 3 is a theoretical mechanism by which water may catalyze the semi-quantitative cracking of the sugar to glycolaldehyde by a retro-aldol reaction.

DETAILED DESCRIPTION OF THE INVENTION

NOTE: In U.S. Pat. No. 5,397,582, issued Mar. 14, 1995, Underwood et al. reported organic concentrations in their product as °Brix values using standard refractory techniques. This unit of measure was developed specifically for sucrose determination. While the refractometric response by weight of glycolaldehyde is comparable to that of glucose on a mass basis, typical impurities like formaldehyde, glyoxal, methyl glyoxal, etc., are known in the analytical community to have much lower responses. One might reasonably expect that with the impurities encountered in sugar thermolysis, °Brix underestimates the total organic solids content. With this caveat the ratio of the weight percent of glycolaldehyde in a solution to its °Brix value provides a rough estimate of the weight ratio of glycolaldehyde to the total organics in solution. The ratio of the weight percent of glycolaldehyde in a solution to its °Brix value shall be referred to as G/B throughout this document and used for purposes of comparison.

Figure 1:
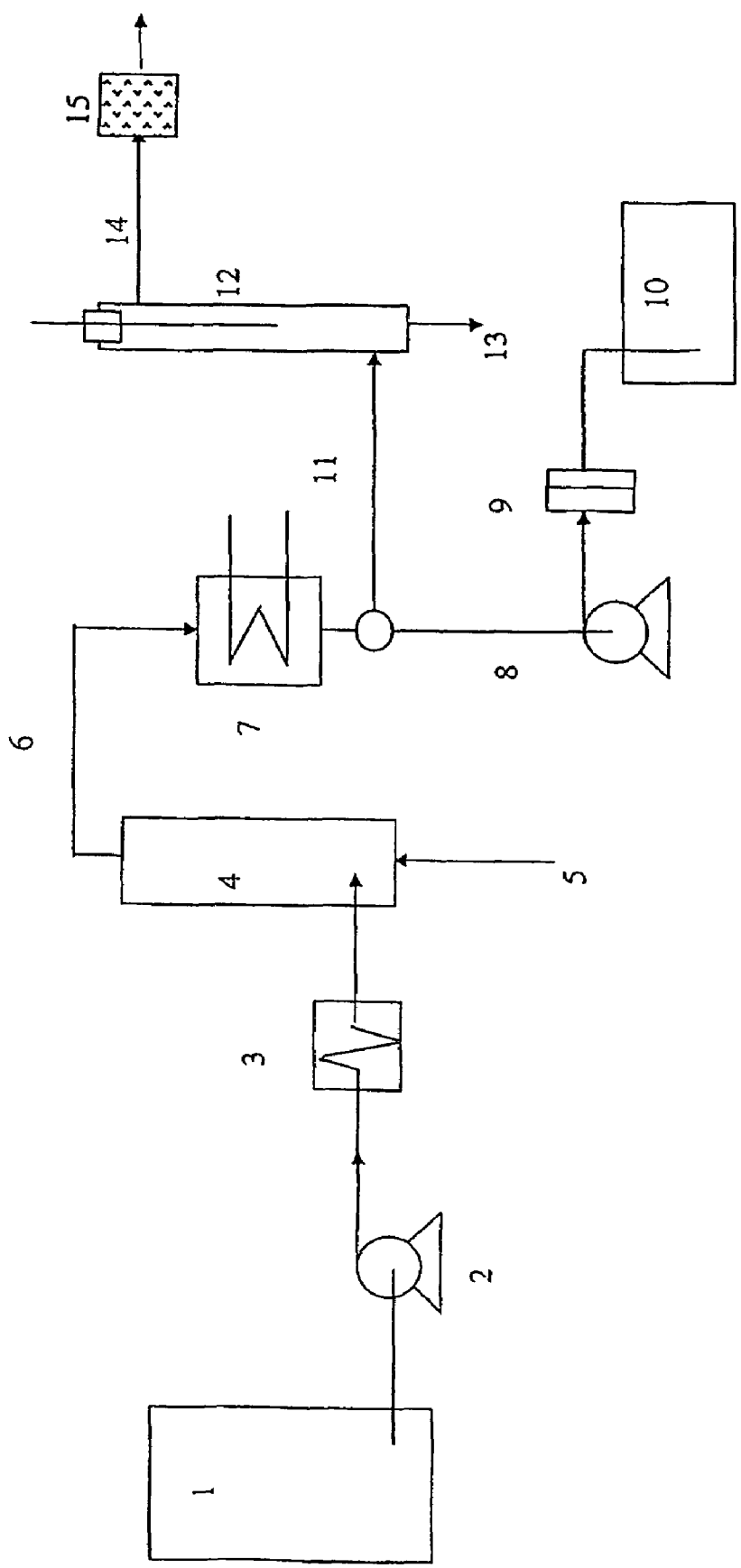
FIG. 1 is an example of an apparatus used to carry out a method of glycolaldehyde production.

The method of production of glycolaldehyde by the hydrous thermolysis of sugars can be carried out using an apparatus as illustrated in FIG. 1. First, an aqueous sugar solution is prepared from an aldose-containing sugar, such as glucose. The aqueous sugar solution is fed from the holding tank 1 via a metering pump 2 into an injector 3. The injector is designed so that the solution is partially vapourized within it and carried into the reactor 4 as a mixture of steam and highly dispersed droplets. The injector 3 may be of any type such that the diameters of the droplets do not exceed 200 microns and most preferably are less than 50 microns. The reactor 4 used is a fluidized bed of sand although any suitable reactor capable of supplying the required heat of vapourization of water and the heat of the thermolysis reaction can be used. A small quantity of inert gas 5 is added to ensure thorough mixing of the sand in the fluidized bed. The inert gas 5 used is nitrogen but it is contemplated that other gases such as additional steam, carbon oxides, or natural gas can be used. The feed stream is heated in the reactor to a temperature in the range of 500–600° C., but preferably in the range 510–560° C. The residence time of the sugar vapour in the high temperature portion of the reactor 4 is approximately one second, with a preferred range of 0.5 to 2 seconds and a maximum range of 0.1 to 5 seconds.

The vapour must be heated for a length of time sufficient to activate the thermolysis reaction. However, excessive residence time will increase the number of secondary decomposition reactions and reduce the final yield. No cyclone is required as the solid soot and char by-product is small, (typically less than 0.2% of the sugar).

The effluent stream 6 from the reactor 4 is condensed in a water-cooled surface condenser 7. Most of the effluent, along with the water vapour, condenses to a liquid solution, which is drawn off by liquid pump 8. The liquid solution is filtered through filter 9 to give the principal product solution, which is then stored in holding tank 10. A small fraction of the effluent (typically only about 3% of the total) does not condense and carried on as an aerosol stream 11 to electrostatic precipitator (EP) 12 where it is coalesced to produce a secondary product liquid stream 13. The secondary product liquid stream 13 is water-poor stream and turns viscous. Additionally, the secondary product liquid stream 13 contains a very small amount of sooty material.

The remaining discharge gas stream 14 consists mainly of the inert gas 5 together with small amounts of product gas. The discharge gas stream 14 is first passed through a column of Drierite™ 15 in order to absorb and measure the amount of any residual water vapour thus improving the calculation of the material balance. Under the best conditions these gases consist mainly of carbon oxides and methane and represent no more than 2–8% by weight of the sugar contained in the aqueous sugar solution. The water content of solutions is determined by Karl-Fischer titration according to well-known and standard protocols.

The illustrative examples, presented below, of hydrous thermolysis were carried out following the above method in the apparatus illustrated in FIG. 1. In all cases, except as otherwise stated, the feed-rate of the aqueous sugar solution was ~2.25 ml/min. and a total of 132 ml (152.9 grams) was fed.

EXAMPLE 1

An aqueous solution of glucose is subjected to hydrous thermolysis in the apparatus described in FIG. 1. The results are collected in Table 1. The feed consisted of an aqueous solution of density 1.158 g/cc containing 34% by weight (anhydrous glucose basis) of Glucose Monohydrate.

The three runs produced on average the extremely low yield of only 0.14 wt % of solids, "char", as filtered out from the condensate. This may be compared with the results of Underwood et al. in U.S. Pat. No. 5,397,582, who obtained 2.5% char from powdered dextrose, some twenty times as much. Between 85–89% of the feed was recovered as condensate. The yield of glycolaldehyde was highest at 528° C. where it was 55% on an anhydrous glucose basis. This may be compared with the yield of only 21.3% from powdered dextrose reported by Underwood et al. The condensate was a clear pale amber solution indicating a lack of coloured contaminants such as furans and like organics.

TABLE 1

Results for Example 1 (Glucose)

| Temperature (° C.) | 528 | 573 |
|---|---|---|
| Product Weights (Grams) | | |
| Condensate | 134.35 | 135.50 |
| EP Catch (~20% water) | 4.43 | 2.90 |
| Drierite (Water Vapour Trap) | 3.70 | 4.53 |
| Gas | 0.27 | 3.19 |
| Losses (mainly water) | 10.11 | 6.74 |
| Concentrations in Condensate (Wt %) | | |
| Water | 64.1 | 65.7 |
| Glyoxal | 1.41 | 1.78 |
| Glycolaldehyde | 21.45 | 19.81 |
| Levoglucosan | Trace | Trace |
| Formaldehyde | 1.66 | 1.90 |
| Acetol | 0.67 | 0.73 |
| Yields (Wt % of Glucose Fed) | | |
| Liquid | 99.49 | 93.85 |
| Glyoxal | 3.64 | 4.64 |
| Glycolaldehyde | 55.44 | 51.64 |
| Formaldehyde | 4.30 | 4.94 |
| Acetol | 1.73 | 1.90 |
| Gas | 0.51 | 6.15 |
| Carbon Monoxide | Trace | 3.97 |
| Ethane | 0 | 0 |
| Ethylene | 0 | 0 |
| Volatile Organics | 0.51 | 2.18 |

A very small amount of darker coloured, viscous, liquid material with low water content (about 20%) was trapped in the electrostatic precipitator 12. As may be seen from Table 1 this was typically around 2% of the condensate amount. While there were some traces of levoglucosan in the EP catch, the amount in the condensate was negligible. Glycolaldehyde, formaldehyde, glyoxal, methylglyoxal and acetol were in effect the only products detectable by liquid chromatography. In the best case, the glycolaldehyde to formaldehyde ratio (G/F) was nearly 13:1.

The data also show that as the temperature is increased there is a greater production of gas with carbon monoxide predominating, at the expense mainly of glycolaldehyde.

EXAMPLE 2

This example illustrates the influence of the chemical character of the sugar on selectivity to glycolaldehyde. The ketose sugar, fructose (Aldrich Chemical Co., 98%), was subjected to hydrous thermolysis in the apparatus of FIG. 1 at varying temperatures. The feed solution was of density 1.146 gram/cm$^3$ and contained 32.45% by weight of fructose. The product from the EP and the condensate were combined to give a total liquid product, the composition of which was then analyzed as a whole. Summary data for the yields on a dry fructose basis are displayed in Table 2.

TABLE 2

Results for Example 2 (Fructose)

| Thermolysis Temp. (° C.) | 571 | 534 |
|---|---|---|
| Yields (Weight % Fructose) | | |
| Gases | 11.79 | 8.77 |
| Solids | Trace | Trace |
| Water | 13.65 | 12.65 |
| Organics | 64.52 | 70.21 |
| Total above Fructose | 89.95 | 91.63 |
| Glyoxal | 2.83 | 3.07 |
| Glyceraldehyde | | 1.55 |
| Methylglyoxal | 10.88 | 6.60 |
| Glycolaldehyde | 21.4 | 12.28 |
| Formaldehyde | 11.61 | 9.83 |
| Acetol | 3.88 | 2.10 |
| Gases | | |
| Carbon Monoxide | 7.10 | 5.70 |
| Carbon Dioxide | Null | Null |
| Methane | 0.24 | Trace |
| Ethene | 0.26 | Trace |
| Volatiles | 4.19 | 3.07 |

There is a dramatic decrease in glycolaldehyde yield, being less than half that of glucose in Example 1. There is also a marked increase in gas production at lower temperatures compared with glucose. There now appears a significant yield of the methylated compounds methylglyoxal and acetol, the latter with an enhanced yield relative to glucose thermolysis at comparable temperatures. Methylglyoxal was not detected from glucose. Most notably formaldehyde production is greatly enhanced both absolutely and relative to glycolaldehyde. The G/F ratio ranged from a low of 1.25:1 to a high of only 1.8:1 in the best case (571° C.).

The condensates ranged in colour from a transparent light yellow liquid at 571° C. to a brownish liquid at 534° C., and were generally significantly darker in colour than those from the glucose thermolysis in Example 1. Qualitative gas chromatography indicates that they contain a significant presence of undesired furanoid compounds including furfural and 5-hydroxymethyl furfural in the 534° C. product.

The conclusion is that keto-sugars (ketoses) are less suitable feedstocks for efficient production of glycolaldehyde by the present method.

EXAMPLE 3

In this example, the disaccharide sucrose, which is a glucosyl fructoside combining the glucose and fructose moieties, is used as a feedstock. Sucrose (Lantic Sugar Ltd.) was subjected to hydrous thermolysis in the apparatus of FIG. 1 at varying temperatures.

TABLE 3

Results for Example 3 (Sucrose)

| | | |
|---|---|---|
| Thermolysis Temp. (° C.) | 550 | 513 |
| Mass of Solution Fed (grams) | 163.0 | 161.0 |
| Products (grams) | | |
| Liquid Condensate | 141.09 | 140.42 |
| EP catch (~20% water) | 7.52 | 8.44 |
| Amount absorbed on Drierite | 4.44 | 4.32 |
| Carbon Monoxide | 3.20 | 2.01 |
| Ethene | 0.10 | |
| Other Volatiles | 2.12 | 0.90 |
| Mass Recovered | 158.57 | 156.0 |
| Concentration in Condensate (Wt %) | | |
| Glyoxal | 0.94 | 1.79 |
| Glycolaldehyde | 13.45 | 12.64 |
| Levoglucosan | Trace | Trace |
| Formaldehyde | 5.15 | 3.47 |
| Acetol | 1.08 | 0.63 |
| Water | 72.5 | 73.0 |
| Total | 93.1 | 91.5 |
| Yields (Wt % Sucrose) | | |
| Glyoxal | 2.43 | 4.76 |
| Glycolaldehyde | 34.74 | 33.60 |
| Levoglucosan | Trace | Trace |
| Formaldehyde | 13.30 | 9.22 |
| Acetol | 2.79 | 1.67 |

The feed solution was of density 1.15 gram/cm$^3$ and contained 34.8% by weight of sucrose. A complete mass balance was carried out and the condensate analyzed to give the results displayed in Table 3.

The greatest yield of glycolaldehyde was obtained at the temperature of 550° C. As the temperature was lowered, the yield of undesirable products such as glyoxal and levoglucosan yields increased noticeably. It may also be seen that the optimal glycolaldehyde yield is intermediate between those for glucose and for sucrose. The results appear to match the expected results if the glucose and fructose moieties in sucrose behaved independently.

This data therefore confirms that aldose sugars like glucose are preferred feedstocks. Nevertheless the yields of glycolaldehyde are impressive and even for this feedstock they exceed all known previous pyrolytic or thermolytic results. However, the G/F ratio was only 3.6:1 in the best case.

EXAMPLE 4

This example pertains to the use of a corn syrup feedstock which provides a mixture of oligosaccharides. This was a preferred feedstock of Underwood et al in U.S. Pat. No. 5,397,582.

The corn syrup sample investigated was a consumer product (BeeHive Best Foods Canada Inc.) which was analyzed for more accurate characterization. The organic solids comprised 60.2, 16.1, 19.4 and 4.3% by weight of oligosaccharides, sucrose, glucose and fructose, respectively, on a water free basis. The composition of the monomeric sugars in the oligosaccharides fraction would be expected to reflect the composition of the cornstarch from which it was derived. There were also unspecified salts present. The sample was diluted to a final solids content of 34.7% and subjected to hydrous thermolysis in the apparatus described in FIG. 1 at the temperature listed in Table 4.

The liquid product had a very dark colour. There was a considerable production of water, indicating extensive occurrence of dehydration reactions. This is consistent with the finding that at the lower temperatures the liquid product contained furfural and 5-hydroxy-methyl furfural in addition to the components listed in Table 4. Furthermore, the production of solids (char) is characteristic of the dehydration of carbohydrates. In addition, levoglucosan (anhydroglucose) and acetic acid were present in significant amounts (not shown). The glycolaldehyde yield was relatively modest, only about 21% of the organic solids fed which is similar to that reported by Underwood et al. (op. cit.) for dextrose powder (glucose).

The product also requires further clean-up prior to use and has an unsatisfactory G/F ratio 2.2:1. This example suggests the conclusion that oligosaccharides and, in particular, those predominant in corn syrup, are not good feedstocks for the hydrous thermolytic production of glycolaldehyde in so far as the both the yield and the relative purity of the product solutions is concerned.

TABLE 4

Results for Example 4 (Corn Syrup)

| | |
|---|---|
| Thermolysis Temp. (° C.) | 550 |
| Yields (Wt % of Corn Syrup Solids) | |
| Char | 4.15 |
| Organics in Solution | 55.53 |
| Water | 20.57 |
| Gas | 18.05 |
| Carbon Monoxide | 7.32 |
| Carbon Dioxide | 6.23 |
| Methane | 0.37 |
| Ethene | 0.30 |
| Other Volatiles | 3.83 |
| Organics Yield | |
| Glyoxal | 2.57 |
| Glycolaldehyde | 20.91 |
| Formaldehyde | 9.44 |
| Acetol | 8.07 |

EXAMPLE 5

It is well known that the scaling-up of a process may produce new and problematic phenomena. For example, especially in thermal decomposition processes, residence time is often a crucial variable as the desired primary reaction 10 product may undergo secondary decomposition. Furthermore, cumulative effects may become manifest during runs over an extended period of time. Glucose (dextrose), the preferred feedstock, was subjected to hydrous thermolysis in a apparatus similar to that shown in FIG. 1 but of approximately twenty times the power of the smaller apparatus used in Example 1. As a consequence of its increased volume, the vapour residence time in the larger reactor was increased to 2–3 seconds. A feed solution containing 50% by weight of dextrose monohydrate (Clintose, ADM Corn Processing Corp.) with a °Brix number of 44.3 was prepared and subjected to hydrous thermolysis in this apparatus at an average rate of 2.8 kg/hr over a period of about 7 hours. The thermolysis temperature was initially at 593° C. but was subsequently decreased to between 530 and 560° C. Instantaneous samples of the condensate were analyzed at intervals of about 45 minutes. Table 5 shows the reactor temperature at the time the sample was collected and the concentrations of the major components in it.

The data show that the process is of high stability and gives nearly optimal results over a considerable temperature range. The final cumulative condensate was a light golden coloured liquid of density 1.126 g/cm³ and a glycolaldehyde concentration of about 25% by weight implying a yield of about 57% on an anhydrous glucose basis. The average G/F ratio was a very satisfactory 11.6:1.

For comparison, a commercial browning agent based on the Maillard reactions of glycolaldehyde, Maillosem was analyzed and found to contain 4.6% by weight of glycolaldehyde, 1.1% of formaldehyde and 0.6% of glyoxal among others, producing a G/F ratio of only 4.2:1. Maillosem also contained small but noticeable amounts of ionic contaminants like chloride, calcium, magnesium, potassium and sodium, among others. In contrast the product solutions of the inventive process are free of all such contaminants when pure glucose is used in the preparation-of the feed solutions.

TABLE 5

Concentrations in Weight % in the Condensate of Example 5 (Dextrose)

| Sample Number | 1 | 2 | 3 | 4 | 5 | 6 | 7 | 8 | 9 |
|---|---|---|---|---|---|---|---|---|---|
| Temp. (° C.) | 593 | 583 | 574 | 558 | 540 | 532 | 543 | 548 | 551 |
| Concentrations (Weight %) | | | | | | | | | |
| Glycoaldehyde | 24.3 | 25.7 | 25.6 | 25.2 | 24.7 | 24.7 | 26.1 | 24.0 | 25.4 |
| Formaldehyde | 2.57 | 2.43 | 2.29 | 2.15 | 2.06 | 2.07 | 2.12 | 1.96 | 1.92 |
| Acetol | 1.65 | 1.51 | 1.43 | 1.08 | 0.86 | 0.93 | 0.79 | 0.78 | 0.75 |
| Glyoxal | 1.63 | 2.10 | 2.21 | 2.48 | 2.72 | 2.93 | 2.57 | 2.53 | 2.44 |

Furthermore, based on its density, a °Brix number for the product was obtained from standard tables (Meade and Chen, "Cane Sugar Handbook", Wiley, N.Y., 1977). The glycolaldehyde to °Brix ratio, G/B, was thereby found to be 0.83. This may be compared to the value of G/B=0.39 obtained by Stradal and Underwood from the pyrolysis of powdered dextrose. The extant results are made more significant when it is considered that the refractometric method used by Underwood et al. in U.S. Pat. No. 5,397,582 to estimate °Brix is likely to underestimate the total organics in solution.

EXAMPLE 6

Using the reactor of Example 5 but with a higher concentration of dextrose as feed solution (54°Brix) and a higher feed rate (7.3 kg of feed solution per hour) gave even higher concentrations and yields of glycolaldehyde product as shown in Table 6.

TABLE 6

Concentrations in Weight % in the Condensate of Example 6 (Dextrose)

| Sample Number | 1 | 2 | 3 |
|---|---|---|---|
| Time (mins.) | 120 | 240 | 348 |
| Temp. (° C.) | 546 | 542 | 540 |
| Concentrations (Weight %) | | | |
| Glycoaldehyde | 38.4 | 39.2 | 40.0 |
| Formaldehyde | 3.3 | 3.1 | 3.5 |
| Acetol | 3.3 | 3.3 | 3.4 |
| Glyoxal | 1.4 | 1.4 | 1.4 |

Figure 4:
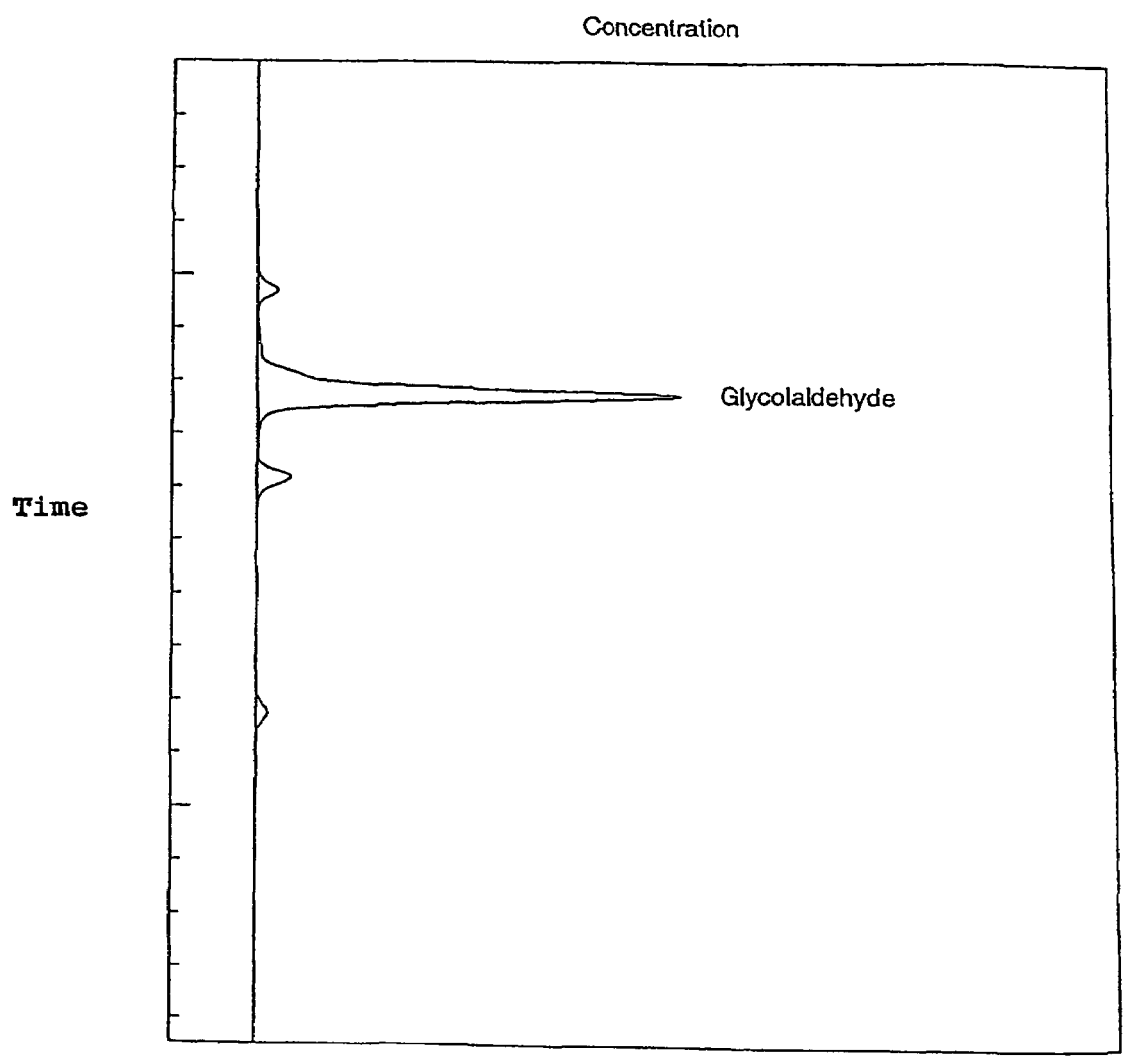
FIG. 4 is a HPLC chromatogram illustrating the purity of the glycolaldehyde solutions produced by the present invention.

A concentration of 40% by weight of glycolaldehyde implies an impressive yield of about 66% on an anhydrous glucose basis. FIG. 4 is a HPLC chromatogram of the product solution, illustrating the purity of the glycolaldehyde product.

EXAMPLE 7

While it is intended that the glycolaldehyde-rich condensates obtained by the present process may be used directly in various applications, nevertheless it may be desirable on occasion to reduce the colour even further. This task is greatly simplified by the low amounts of impurities as evidenced by their pale colours and high G/B ratios.

Various methods may be employed for this purpose, such as those described by Scott ("Chemicals and Fuels from Biomass Flash Pyrolysis", DSS Contract 38ST 23216-6-6164, Renewable Energy Branch, Energy Mines and Resources Canada, Ottawa, Canada, February 1988), namely use of ion-exchange resins, solvent extraction with methylene chloride and use of activated carbon. Activated carbon was found to be particularly suited for this purpose as it shows high selectivity for the colour components over glycolaldehyde.

When 137 grams of the condensate from Example 1 was stirred with 17 grams of a commercial activated carbon (available from Calgon Carbon Corporation) at room temperature for 30 minutes, the colour was completely removed while the glycolaldehyde concentration decreased only slightly, from 25% to 24.2%. The use of adsorption on activated carbon therefore provides a simple and inexpensive method to decolorize the product.

While in no way meant to be a limitation of the mechanism involved, there is a theoretical basis for the results achieved. There is recent precedent for the recognition that water may play a reactive role in the thermal decomposition of carbohydrate materials. A recent study of the pyrolysis of cellulose proposes that water is not an inert spectator as previously thought, but rather plays a chemical role. In particular, it functions as a weak nucleophile that promotes cross-linking and subsequent char formation at the expense of depolymerization. The reaction is thought to proceed through a carbonium ion intermediate. Indeed, water is well known to be weakly amphoteric and can therefore provide both electrophilic and nucleophilic moieties. Since it is likely that fragmentation of sugars would proceed by a first ring-opening step followed by scission of the resulting chain form, it seems possible that water may play a similar chemical role in the process of the invention. One hypothetical mechanism, adapted from Ball et al. (R. Ball, A. C. McIntosh and J. Brindley, "The role of char-forming processes in the thermal decomposition of cellulose", Phys.

Chem. & Chem. Phys., Vol. 1, 5035–5043, 1999) for such a process is illustrated in FIG. 2.

Water may also play a role in the subsequent chain scission process. Richards proposed a concerted retro-Diels-Alder mechanism involving an initial dehydration step as a source of glycolaldehyde in cellulose decomposition. This seems unlikely to be operative in the inventive process since the yield of glycolaldehyde would not then be expected to exceed 33%. In fact, the accepted mechanism for sugar fragmentation among the experts in food browning is retro-aldolization of the open chain form of the sugar. Thus, aldose sugars are expected to be particularly suitable as feedstocks as they provide a terminal aldehydes group in the open chain form. Again, on account of its amphoteric character, water may catalyze this process as well especially at the high temperatures likely to be encountered in the inventive process.

A possible mechanism is illustrated in FIG. 3, which is based on a mechanism proposed by Namiki and Hayashi in their review of the early stages of the Maillard reaction (Agric. Biol. Chem., Vol. 50 (8), 1965–1970, 1986). Shown is the removal of the first molecule of glycolaldehyde from the sugar. It may be seen that the residue is terminated by an aldehydic group and the process may repeat. Thus, at least in principle, a maximum glycolaldehyde yield of 100% from aldose sugars would be possible.

Furthermore, use of solutions of sugars reduces the concentration of sugar molecules in the pyrolyzing droplets of solution and thereby reduces the probability for undesirable inter-molecular reactions. The proportion of water in the aqueous sugar solution may be in the range of 25–99% with a preferred range of 30–70% by weight.

Finally, Richards et al. have recently disclosed (G. N. Richards et al. "Preparation of Trisaccharides and Polymers by Pyrolysis of Amorphous Cellulose", U.S. Pat. No. 5,206, 355, 1993) that the pyrolysis product distribution from certain sugars was modified when amorphous rather than crystalline sugars were pyrolyzed. In this case, amorphous sucrose was obtained by slow low temperature evaporation of water. It may well be that in the present invention, the sugars are rendered amorphous when water evaporates from the droplets.

While these speculations suggest possible reasons for the results achieved, it is recognized that other hitherto unrecognized effects may also play a significant role.

High concentrations of water may also provide the further process benefit that the efficiency of the surface condensers is improved such that most of the product may be collected in a single surface condenser. This enables the use of heat exchangers to recover most of the thermal energy supplied such that there is no significant penalty in energy consumption associated with the vapourization of large amounts of water.

An aspect of its behaviour that must be borne in mind in the reduction of the invention to practice is the propensity of glycolaldehyde to undergo further unimolecular decomposition to lower molecular weight gases, upon its prolonged exposure to heat. Thus, as is well known in the art, although the optimal temperature appears to be in the range 500–575° C., the overall yields will be strongly influenced by the residence time effects. In studies of glycolaldehyde production by pyrolysis of cellulose Radlein et al. ("Fast pyrolysis of natural polysaccharides as a potential industrial process", J. Anal. Appl. Pyrol. Vol. 19, 41–63, 1991) noted that the yield of glycolaldehyde increased from a few percent at 400° C. through a maximum at about 600° C. beyond which it fell sharply. This indicates that secondary decomposition reactions of glycolaldehyde proceed very rapidly beyond this latter temperature and thus that a practitioner of the invention should endeavour to design the apparatus in such a way as to minimize the exposure of the products to excessive temperatures, certainly no more than 600° C., for extended periods of time. For example, this might be achieved in an adiabatic reactor in which heat is only delivered in the reaction zone. Then, since secondary decomposition reactions of typical biomass pyrolysates are known to be endothermic, such undesirable reactions would tend to cool the effluent and be in effect self-quenching. Residence times are generally in the range 0.1–5 seconds, but preferably in the range 0.5 to 2 seconds.

Although significant quantities of water must be evaporated in the process, the energy requirements of the process may be substantially reduced by using heat recovery techniques well known in the engineering community, since standard surface condensers may be applied for cooling the product stream. This is in contrast to most biomass pyrolysis processes which, on account of high aerosol loading and product chemical instability, are usually cooled by rapid mixing with a cold stream. Useful heat recovery is ruled out in such cases.

Accordingly, while this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is therefore contemplated that the appended claims will cover any such modifications or embodiments as fall within the true scope of the invention.

We claim:

1. A method for the production of glycolaldehyde by hydrous thermolysis comprising the steps of:
    a) preparing an aqueous sugar solution, from an aldose-containing sugar selected from the group consisting of glucose and sucrose;
    b) atomizing said aqueous sugar solution;
    c) injecting said atomized aqueous sugar solution into a reactor heated between 500 and 600° C., creating a vaporous pyrolysis product;
    d) cooling said vapourous pyrolysis product in a condenser, obtaining a liquid condensate;
    e) collecting said liquid condensate into a holding tank to yield a glycolaldehyde-rich liquid; and
    f) filtering the glycolaldehyderich liquid, wherein the resulting yield of glycolaldehyde is at least 30% by weight of the sugar used in the aqueous solution.

2. The method of claim 1, including an additional step (g), wherein said glycolaldehyde-rich liquid is contacted by activated carbon to remove coloured organic components.

3. The method of claim 1, wherein said aqueous sugar solution contains water in the range of 25% to 99% by weight.

4. The method of claim 1, wherein said aqueous sugar solution contains water in the range of 30% to 70% by weight.

5. The method of claim 1, wherein said atomized aqueous sugar solution has droplets of a diameter less than 200 microns.

6. The method of claim 1, wherein said atomized aqueous sugar solution has droplets of a diameter less than 50 microns.

7. The method of claim 1, wherein said reactor is heated to a temperature in the range of 520 to 560° C.

8. The method of claim 1, including filtering said liquid LO condensate after said cooling step and before collecting in said holding tank.

9. The method according to claim 1, wherein the glycolaldehyde-rich liquid of step (e) has a glycolaldehyde percentage by weight to °Brix ratio greater than 0.5.

10. The method according to claim 2, wherein the glycolaldehyde-rich liquid of step (e) has a glycolaldehyde percentage by weight to °Brix ratio greater than 0.5.

11. A method for the production of glycolaldehyde by hydrous thermolysis comprising the steps of:
  a) preparing an aqueous sugar solution from glucose containing water in the range of 30% to 70% by weight;
  b) atomizing said aqueous sugar solution into droplets of a diameter of less than 50 microns;
  c) injecting said atomized aqueous sugar solution into a reactor heated between 520 and 560° C., creating a vapourous pyrolysis product;
  d) cooling said vapourous pyrolysis product in a condenser, obtaining a liquid condensate;
  e) collecting said liquid condensate into a holding tank to yield a glycolaldehyde-rich liquid; and
  f) filtering said glycolaldehyde-rich liquid, wherein the resulting yield of glycolaldehyde is at least 50% by weight of the glucose used in the aqueous solution.

12. The method of claim 11, including an additional step (g), wherein said glycolaldehyde-rich liquid is contacted by activated carbon to remove coloured organic components.

* * * * *